United States Patent
Lindqvist

[11] Patent Number: 6,098,623
[45] Date of Patent: Aug. 8, 2000

[54] PRESSURE-LIMITING VALVE WHEREIN VALVE PLATE OSCILLATIONS ARE PREVENTED

[75] Inventor: Bjorn Lindqvist, Lidingo, Sweden

[73] Assignee: Siemens Elema AB, Solna, Sweden

[21] Appl. No.: 09/174,899

[22] Filed: Oct. 19, 1998

[30] Foreign Application Priority Data

Oct. 20, 1997 [SE] Sweden .................................. 9703810

[51] Int. Cl.[7] .................................................. A61M 15/00
[52] U.S. Cl. ................................ 128/205.24; 128/203.24; 128/207.16; 137/541
[58] Field of Search .......................... 128/205.24, 207.12, 128/207.16; 137/543.21, 543.23; 251/128, 118

[56] References Cited

U.S. PATENT DOCUMENTS 3,780,760  12/1973  Berner .
4,056,121  11/1977  Gerdes ..................................... 137/541
4,454,893  6/1984   Orchard ............................. 128/205.24
5,199,769  4/1993   Beck et al. .
5,687,709  11/1997  Akerberg ............................ 128/203.12
5,890,513  4/1999   Di Stefano ............................. 137/547

FOREIGN PATENT DOCUMENTS 0 139 363   5/1985   European Pat. Off. .

*Primary Examiner*—John G. Weiss
*Assistant Examiner*—V. Srivastava
*Attorney, Agent, or Firm*—Hill & Simpson

[57] ABSTRACT

A pressure-limiting valve for use in a gas system for manual ventilation of patients, has a valve seat with an opening, a valve plate and a force-generating element, the force-generating element being arranged to press the valve plate against the valve seat in order to close the opening. In order to reduce the risk of annoying noise from the valve, the valve is devised so the valve plate is asymmetrically shaped, so as to cause a gas flowing through the opening in the valve seat, when the valve is in the open position, to apply an asymmetrical force against the valve plate.

9 Claims, 1 Drawing Sheet

PRESSURE-LIMITING VALVE WHEREIN VALVE PLATE OSCILLATIONS ARE PREVENTED

BACKGROUND OF THE INVENTION

1. Field of the Invention

The present invention is directed to a pressure-limiting valve for use in a gas system, such as for manual ventilation of a patient.

2. Description of the Prior Art

Manual ventilation of patients is very common in conjunction with anaesthesia administration. Physicians employ manual ventilation of the patient especially at the start and end of anaesthetization. The physician then uses a manually operated gas system, with a hand ventilator and an adjustable, pressure-limiting valve for controlling the pressure of the breathing gas in the manually operated gas system. The adjustable pressure-limiting valve is often referred to as an APL valve, the term that will be used henceforth in this description.

In principle, the APL valve includes a valve seat and a valve plate which, in the closed position, seals against the valve seat and which is lifted by positive pressure off the valve seat to release surplus gas. An adjustable valve spring exerts pressure on the valve plate with a force corresponding to the pressure set by the physician. Since the APL valve must open to release surplus gas at low positive pressures (about 3 cmH$_2$O above atmospheric pressure), the force on the valve plate must not be too large at the start of the setting range. In principle, the APL valve should not offer more resistance than is necessary to enable the hand ventilator just to be filled. In particular, it must not pose major resistance to patient expirations. One problem that can develop with APL valves is that they can begin oscillating, under certain flow and external conditions (with tubes, lines, other valves etc.), in such a way that an annoying noise is generated.

SUMMARY OF THE INVENTION

An object of the present invention is to provide a valve that greatly reduces the risk of the aforementioned noise occurring.

The above object is achieved in accordance with the principles of the present invention in a pressure-limiting valve for use in a gas system for manual ventilation of a patient, having a valve seat with an opening therein, a valve plate disposed on said valve seat, and a force-generating element acting on said valve plate, the force-generating element pressing said valve plate against the valve seat to close the opening, wherein the valve plate is asymmetrical so that a gas flowing through the opening in the valve seat, when the valve is open, exerts an asymmetrical force against the valve plate.

The problem of noise is greatly reduced by the valve plate design which causes the force exerted by flowing gas on the valve plate to be applied asymmetrically. Asymmetrical application reduces the tendency of the valve to self-oscillate, especially if the asymmetry is selected in relation to the gas flows that will be passing the valve. Moreover, the valve plate will not move synchronously up and down with its entire contact surface pressing on the valve seat but will actually describe a wave-like motion.

The effect is accentuated when the valve plate is shaped so a lateral force is generated.

Since the valve opens at a low pressure, the mass of the valve plate can, in principle, serve as the valve's closing force. When the pressure needs to be adjusted, a spring can contribute increased pressures.

DESCRIPTION OF THE PREFERRED EMBODIMENTS

Figure 1:
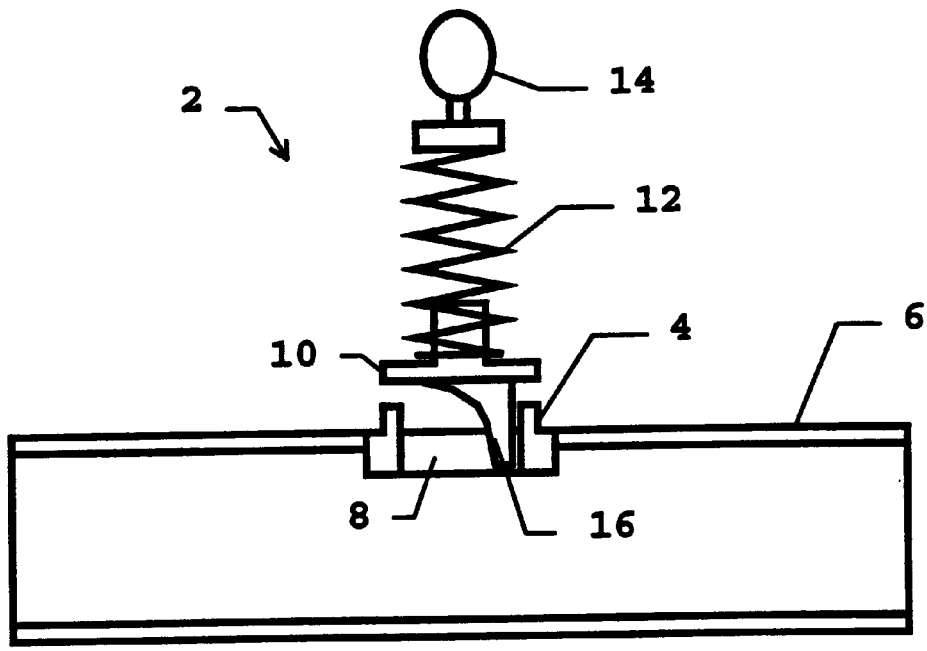
FIG. 1 shows a first embodiment of a valve according to the invention.

The valve 2 in FIG. 1 has a valve seat 4 arranged in a tube 6 for breathing gas in a gas system for manual ventilation of a patient. An opening 8 in the valve seat 4 allow gas to pass when the valve 2 is open. A valve plate 10 is arranged against the valve seat 4 to close the valve 2 with an adjustable pressure. Here, the valve plate 10 is pressed against the valve seat 4 by a spring 12 whose force is manually adjustable with a knob 14. The valve plate 10 is devised with a projection 16, which extends into the opening 8 in the valve seat 4, impeding/preventing gas from flowing past on the side of the valve plate 10 on which the projection 16 is arranged, to prevent gas flowing from the tube 6 up through the opening 8 from causing annoying noise in the valve 2 and its surroundings. This generates a lateral force which opposed self-oscillation and also ensures that the valve plate 10 is not raised and lowered parallel to the valve seat 4.

The valve 2 can also have additional components in order to protect, control and take part in its normal operation in some other way. Since the invention does not affect these parts of the valve 2, they are not included in FIG. 1 (or FIG. 2).

Figure 2:
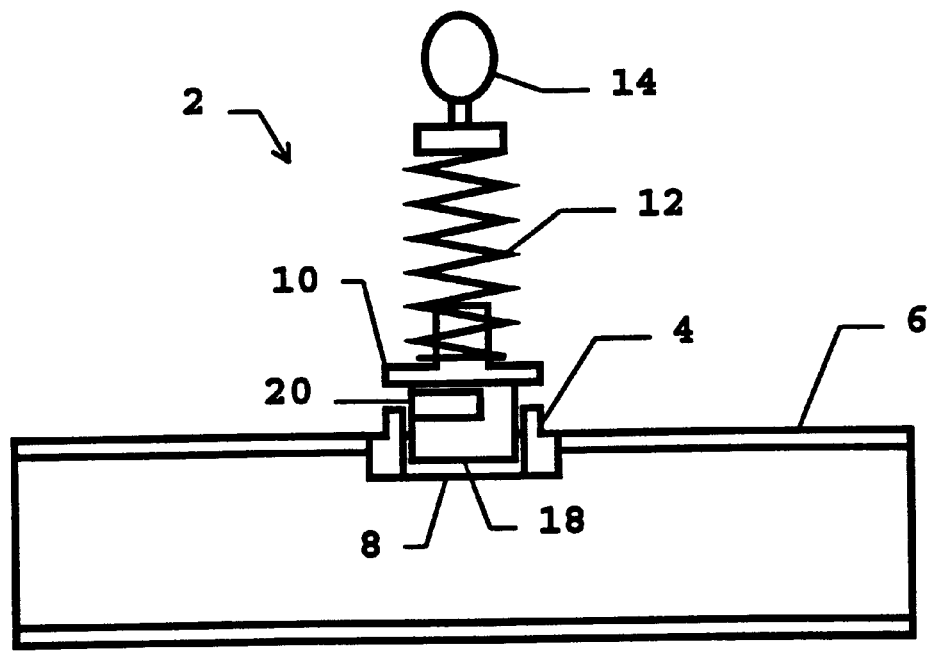
FIG. 2 shows a second embodiment of a valve according to the invention.

FIG. 2 shows another version of the valve 2. Identical components have' been assigned the same designations. The only difference is that the valve plate 10 in FIG. 2 has a projection in the form of a cylindrical tube 18 in which an opening 20 carries gas out through the valve 2. Channeling the path of gas flow generates a lateral force that is exerted on the valve plate 10.

In positions in which small increases exceeding atmospheric pressure are intended to be able to open the valve, the mass of the valve plate is sufficient, in principle, to provide an adequate closing force. A manual increase in force is then only needed for increased pressures.

The projections 16, 18 in FIGS. 1 and 2 should not constitute obstacles greater than the equivalent of 180° of the circumference of the valve plate 10.

Alternative designs are feasible. For example, the tube 18 in FIG. 2 can be devised to encircle the valve seat 4 instead of projecting through the opening 8.

Asymmetrical distribution of the valve plate's mass is sufficient to oppose self-oscillation and can also cause the valve plate 10 to describe a wave motion on the valve seat 2, instead of just moving straight up and down, thereby damping the noise generated when the valve 2 closes.

The most important aspect of the invention is the design of the valve plate 10 so an asymmetrically distributed force is applied to it when the valve opens to release gas.

Although modifications and changes may be suggested by those skilled in the art, it is the intention of the inventor to embody within the patent warranted hereon all changes and modifications as reasonably and properly come within the scope of his contribution to the art.

I claim as my invention:

1. A pressure-limiting valve for use in a gas system for manual ventilation of a patient, comprising:

a valve seat having an opening therein;

a valve plate mounted for movement toward and away from said valve seat to open and close said valve opening;

a force-generating element acting on said valve plate to urge said valve plate toward said opening; and said valve plate having a projection which gives said valve plate an asymmetrical shape for causing a gas flow through said opening in said valve seat, when said opening is open, to exert an asymmetrical force on said valve plate.

2. A valve as claimed in claim 1 wherein said opening in said valve seat is oriented to face upwardly, and wherein said force-generating element comprises said valve plate, with a closing force acting on said valve plate being generated by gravity.

3. A valve as claimed in claim 1 wherein said force-generating element comprises a pressure-exerting spring disposed to urge said valve plate against said valve seat.

4. A valve as claimed in claim 1 wherein said valve plate comprises a circular disk with an asymmetrically disposed projection thereon projecting toward said valve seat.

5. A valve as claimed in claim 4 wherein said projection has an exterior which fits inside said opening in said valve seat when said valve plate closes said valve opening.

6. A valve as claimed in claim 4 wherein said projection comprises a truncated cylindrical circular segment having a base angle of less than 180°.

7. A valve as claimed in claim 1 wherein said valve plate comprises a circular disk with a tubular cylinder attached thereto, forming said projection, said tubular cylinder having a cylinder wall with an opening therein, said cylinder extending toward said valve seat.

8. A valve as claimed in claim 7 wherein said cylinder has an exterior which fits in said opening in said valve seat when said valve plate closes said opening.

9. A valve as claimed in claim 7 wherein said opening in said cylinder wall comprises a circular arc having an aperture angle larger than 180°.

* * * * *